United States Patent [19]

Ogihara et al.

[11] Patent Number: 5,498,737
[45] Date of Patent: Mar. 12, 1996

[54] SILACYCLOHEXANE COMPOUND, A METHOD OF PREPARING IT AND A LIQUID CRYSTAL COMPOSITION CONTAINING IT

[75] Inventors: Tsutomu Ogihara; Takaaki Shimizu; Takeshi Kinsho; Tatsushi Kaneko; Ryuichi Saito, all of Kubiki; Hideshi Kurihara, Kawasaki, all of Japan

[73] Assignee: Shin-Etsu Chemical Co., Ltd., Tokyo, Japan

[21] Appl. No.: 377,961

[22] Filed: Jan. 25, 1995

[30] Foreign Application Priority Data

Jan. 28, 1994 [JP] Japan ................... 6-024991

[51] Int. Cl.⁶ ...................................... C07F 7/08
[52] U.S. Cl. ............... 556/406; 252/299.6; 252/299.63
[58] Field of Search ................................ 556/406

[56] References Cited

U.S. PATENT DOCUMENTS

| | | | |
|---|---|---|---|
| 4,826,984 | 5/1989 | Berlin et al. | 556/406 X |
| 4,973,723 | 11/1990 | Cawthon et al. | 556/406 |

FOREIGN PATENT DOCUMENTS

| | | |
|---|---|---|
| 0125563 | 5/1984 | European Pat. Off. . |
| 0355008 | 8/1989 | European Pat. Off. . |
| 0630903 | 6/1994 | European Pat. Off. . |

*Primary Examiner*—Paul F. Shaver
*Attorney, Agent, or Firm*—Townsend & Banta

[57] ABSTRACT

A silacyclohexane compound represented by the following general formula (1):

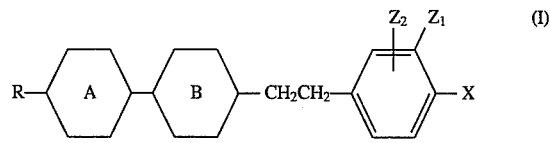

wherein R denotes a linear-chain alkyl group with a carbon number of 1–10, a mono- or di-fluoroalkyl group with a carbon number of 1–10, a branched-chain alkyl group with a carbon number of 3–8, an alkoxyalkyl group with a carbon number of 2–7, or an alkenyl group with a carbon number of 2–8, and at least one of

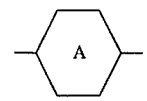

and

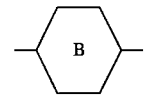

denotes a trans-1-sila-1,4-cyclohexylene or a trans-4-sila-1,4-cyclohexylene group whose silicon at position 1 or position 4 has a substitutional group(s) of H, F, Cl or $CH_3$ and the other is a trans-1,4-cyclohexylene group, X denotes a CN, F, F, Cl, $CF_3$, $OCF_3$, $OCHF_2$, $OCHFCl$, $CF_2Cl$, $OCF_2Cl$, R or OR group, $Z_1$ denotes H, F or Cl, and $Z_2$ denotes H or F.

7 Claims, No Drawings

SILACYCLOHEXANE COMPOUND, A METHOD OF PREPARING IT AND A LIQUID CRYSTAL COMPOSITION CONTAINING IT

BACKGROUND OF THE INVENTION

1. Field of the invention

This invention relates to a new silacyclohexane compound, a method of preparing it, and a liquid crystal composition which contains it, as well as a liquid crystal display element containing said liquid crystal composition.

2. The Prior Art

A liquid crystal display element utilizes the optical anisotropy and dielectric anisotropy of liquid crystal substances. Display methods include the TN mode (twisted nematic mode), the STN mode (super twisted nematic mode), the SBE mode (super birefringence mode), the DS mode (dynamic scattering mode), the guest-host mode, the DAP mode ("deformation of aligned phase" mode), the PD mode (polymer dispersion mode) and the OMI mode (optical mode interference mode). The most common display device has a twisted nematic structure based on the Schadt-Helfrich mode.

The properties required of the liquid crystal substance used in these liquid crystal displays are somewhat different depending on the display method. However, a wide liquid crystal temperature range and stability with regard to moisture, air, light, heat, electric fields, etc., are properties commonly required by all display methods. Furthermore, it is desirable for the liquid crystal material to have a low viscosity, and also to have a short address time, low threshold voltage and high contrast in the cell(s).

Currently, there is no single compound which satisfies all these requirements. In practice, liquid crystal mixtures are used which are obtained by mixing several to more than ten liquid crystal compounds and latent liquid crystal compounds. Because of this, it is also important that the components of a liquid crystal composition mix easily.

Among liquid crystal compounds which can be these components, one of the basic components conventionally known which controls the electro-optical performance is a compound which has the cyclohexyl ring-cyclohexyl ring-ethylene-phenyl structure (ECCP structure) such as shown below.

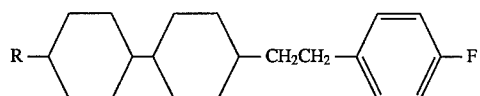

(See EP-125563)

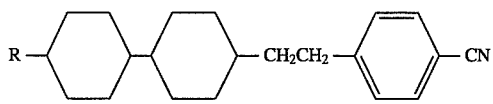

(See EP-125563)

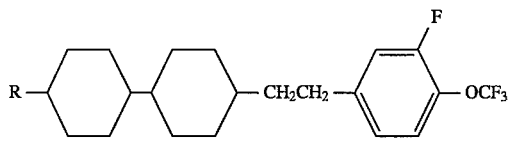

(See Japanese unexamined patent publication Tokuhyo Hei 4-501575)

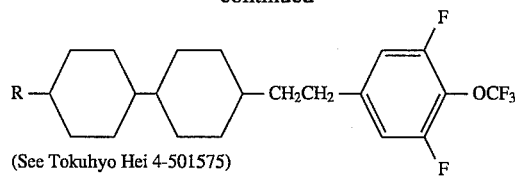

(See Tokuhyo Hei 4-501575)

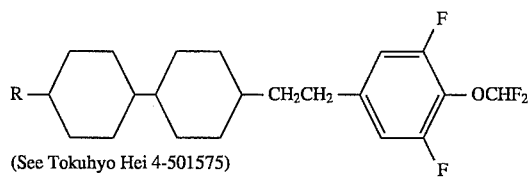

(See Tokuhyo Hei 4-501575)

In recent years, along with the expansion of the applications of liquid crystal displays, the characteristics required of liquid crystal materials are becoming more and more advanced and demanding. In particular, superior characteristics such as improved low temperature performance, a wider temperature range for automobile onboard use and a lower driving voltage, compared with conventional liquid crystal substances, are desired.

BRIEF SUMMARY OF THE INVENTION

From such a viewpoint, this invention is a newly developed liquid crystal substance targeting improvement in the characteristics of liquid crystal substances, and its object is to provide a liquid crystal compound containing silacyclohexane rings, which is completely different from the conventional liquid crystal compounds with the aforementioned cyclohexyl ring-cyclohexyl ring-ethylene-phenyl structure (ECCP structure).

That is, this invention is a silacyclohexane compound represented by the following general formula (I).

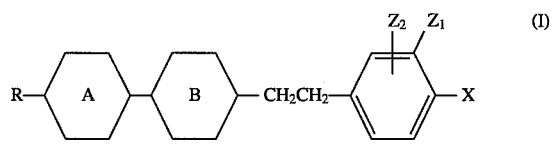

In this formula, R denotes a linear-chain alkyl group with a carbon number of 1–10, a mono- or di-fluoroalkyl group with a carbon number of 1–10, a branched-chain alkyl group with a carbon number of 3–8, an alkoxyalkyl group with a carbon number of 2–7, or an alkenyl group with a carbon number of 2–8. For

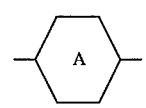

and

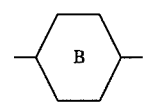

at least one of the two denotes a trans-1-sila-1,4-cyclohexylene or a trans-4-sila-1,4-cyclohexylene group whose silicon at position 1 or position 4 has a substitutional group(s) of H, F, Cl or $CH_3$ and the other is a trans-1,4-cyclohexylene group. X denotes a CN, F, Cl, $CF_3$, $OCF_3$, $OCHF_2$, OCHFCl, $CF_2Cl$, $OCF_2Cl$, R or OR group. $Z_1$ denotes H, F or Cl. $Z_2$ denotes H or F.

This invention is also a method of preparing the silacyclohexane compound as represented by said general formula (I) characterized by the use of a carbon-carbon bond formation reaction or a carbon-silicon bond formation reaction between an organometallic reagent

R—M (M denotes MgP (P denotes a halogen atom), ZnP or Li) and

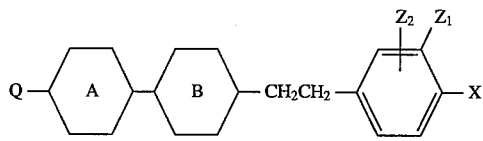

(Q denotes a halogen atom, or an alkoxy, methanesulfonyl, trifluoromethanesulfonyl, benzenesulfonyl or p-toluenesulfonyl group).

This invention is also a method of preparing the silacyclohexane compound as represented by said general formula (I) characterized by the use of a carbon-carbon bond formation reaction or a carbon-silicon bond formation reaction between an organometallic reagent

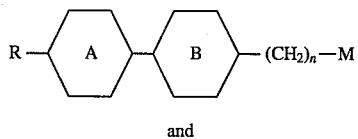

and

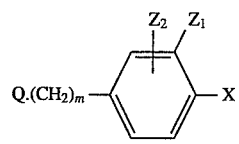

(Each of n and m denotes an integer 0, 1 or 2 where n+m=2).

This invention is also a method of preparing the silacyclohexane compound as represented by said general formula (I) characterized by the use of a carbon-carbon bond formation reaction or a carbon-silicon bond formation reaction between an organometallic reagent

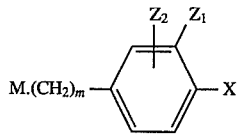

and

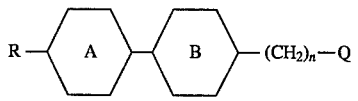

This invention is also a method of preparing the silacyclohexane compound as represented by said general formula (I) characterized by the use of a carbon-carbon bond formation reaction or a carbon-silicon bond formation reaction between an organometallic reagent

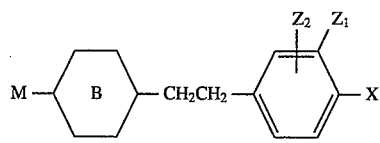

and

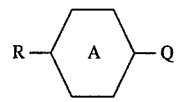

This invention is also a method of preparing the silacyclohexane compound as represented by said general formula (I) characterized by the use of a carbon-carbon bond formation reaction or a carbon-silicon bond formation reaction between an organometallic reagent

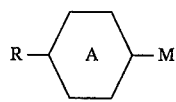

and

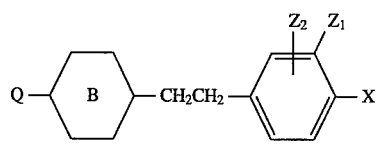

Furthermore, this invention is a liquid crystal composition characterized by containing the compound as represented by the general formula (I) and a liquid crystal display element characterized by containing this liquid crystal composition.

DETAILED DESCRIPTION

The new compounds represented by said general formula (I) are silacyclohexane compounds whose ring structure has at least one trans-1 or trans-4-silacyclohexane ring, specifically represented by ring structures shown below:

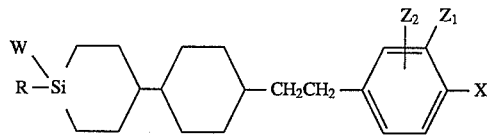

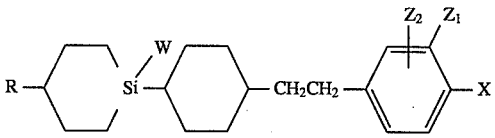

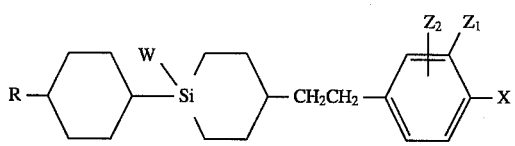

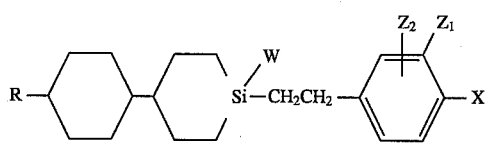

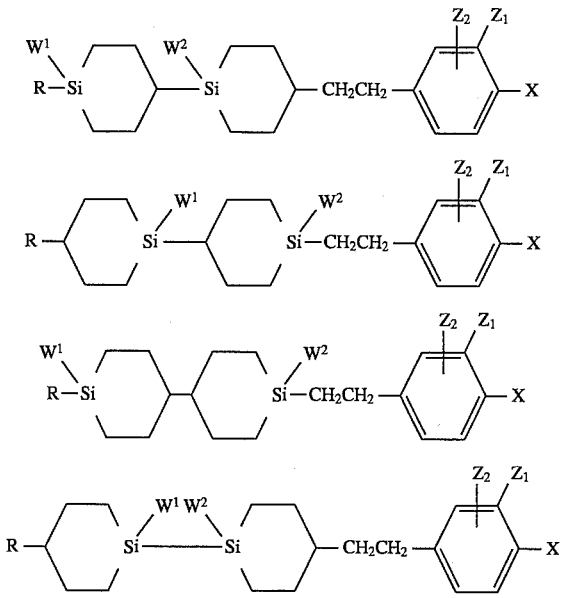

In these formulas, R denotes the following groups in (a) through (e):

(a) A linear-chain alkyl group with a carbon number of 1–10, i.e. a methyl, ethyl, n-propyl, n-butyl, n-pentyl, n-hexyl, n-heptyl, n-octyl, n-nonyl or n-decyl group (b) A mono- or di-fluoroalkyl group with a carbon number of 1–10, i.e. fluoromethyl, 1-fluoroethyl, 1-fluoropropyl, 1-fluorobutyl, 1-fluoropentyl, 1-flurorhexyl, 1-fluoroheptyl, 1-fluorooctyl, 1-fluorononyl, 1-fluorodecyl, 2-fluoroethyl, 2-fluoropropyl, 2-fluorobutyl, 2-fluoropentyl, 2-fluorohexyl, 2-fluoroheptyl, 2-fluorooctyl, 2-fluorononyl, 2-fluorodecyl, 3-fluoropropyl, 3-fluorobutyl, 3-fluoropentyl, 3-fluorohexyl, 3-fluoroheptyl, 3-fluorooctyl, 3-fluorononyl, 3-fluorodecyl, 4-fluorobutyl, 4-fluoropentyl, 4-fluorohexyl, 4-fluoroheptyl, 4-fluorooctyl 4-fluorononyl, 4-fluorodecyl, 5-fluoropentyl, 5-fluorohexyl 5-fluoroheptyl, 5-fluorooctyl, 5-fluorononyl, 5-fluorodecyl 6-fluorohexyl, 6-fluoroheptyl, 6-fluorooctyl, 6-fluorononyl 6-fluorodecyl, 7-fluoroheptyl, 7-fluorooctyl, 7-fluorononyl 7-fluorodecyl, 8-fluorooctyl, 8-fluorononyl, 8-fluorodecyl, 9-fluorodecyl, 10-fluorodecyl, difluoromethyl, 1,1-difluoroethyl, 1,1-difluoropropyl, 1,1-difluorobutyl, 1,1-difluoropentyl, 1,1-difluorohexyl, 1,1-difluoroheptyl, 1,1-difluorooctyl, 1,1-difluorononyl, 1,1-difluorodecyl, 2,2-difluoroethyl, 2,2-difluoropropyl, 2,2-difluorobutyl, 2,2-difluoropentyl, 2,2-difluorohexyl, 2,2-difluoroheptyl, 2,2-difluorooctyl, 2,2-difluorononyl, 2,2-difluorodecyl, 3,3-difluoropropyl, 3,3-difluorobutyl, 3,3-difluoropentyl, 3,3-difluorohexyl, 3,3-difluoroheptyl, 3,3-difluorooctyl, 3,3-difluorononyl, 3,3-difluorodecyl, 4,4-difluorobutyl, 4,4-difluoropentyl, 4,4-difluorohexyl, 4,4-difluoroheptyl, 4,4-difulorooctyl, 4,4-difluorononyl, 4,4-difluorodecyl, 5,5-difluoropentyl, 5,5-difluorohexyl, 5,5-difluoroheptyl, 5,5-difluorooctyl, 5,5-difluorononyl, 5,5-difluorodecyl, 6,6-difluorohexyl, 6,6-difluoroheptyl, 6,6-difluorooctyl, 6,6-difluorononyl, 6,6-difluorodecyl, 7,7-difluoroheptyl, 7,7-difluorooctyl, 7,7-difluorononyl, 7,7-difluorodecyl, 8,8-difluroctyl, 8,8-difluorononyl, 8,8-difluorodecyl, 9,9-difluorononyl or 10,10-difluorodecyl group (c) A branched-chain alkyl group with a carbon number of 3–8, i.e. an isopropyl, sec-butyl, isobutyl, 1-methylbutyl, 2-methylbutyl, 3-methylbutyl, 1-methylpentyl, 2-methylpentyl, 3-methylpentyl, 1-ethylpentyl, 1-methylhexyl, 2-methylhexyl, 3-methylhexyl, 2-ethylhexyl, 3-ethylhexyl, 1-methylheptyl, 2-methylheptyl or 3-methylheptyl group (d) An alkoxyalkyl group with a carbon number of 2–7, i.e. a methoxymethyl, ethoxymethyl, propoxymethyl, butoxymethyl, pentoxymethyl, hexyloxymethyl, methoxyethyl, ethoxyethyl, propoxyethyl, butoxyethyl, pentoxyethyl, methoxypropyl, ethoxypropyl, propoxypropyl, butoxypropyl, methoxybutyl, ethoxybutyl, propoxybutyl, methoxypentyl or ethoxypentyl group (e) An alkenyl group with a carbon number of 2–8, i.e. a vinyl, 1-propenyl, allyl, 1-butenyl, 3-butenyl, isoprenyl, 1-pentenyl, 3-pentenyl, 4-pentenyl, dimethylallyl, 1-hexenyl, 3-hexenyl, 5-hexenyl, 1-heptenyl, 3-heptenyl, 6-heptenyl or 7-octenyl group W, $W^1$ and $W^2$ independently denote H, F, Cl or $CH_3$.

X denotes a CN, F, Cl, $CF_3$, $OCF_3$, $OCHF_2$, OCHFCl, $CF_2Cl$, $OCF_2$ Cl, R or OR group.

$Z_1$ denotes H, F or Cl. $Z_2$ denotes H or F.

Specific examples of

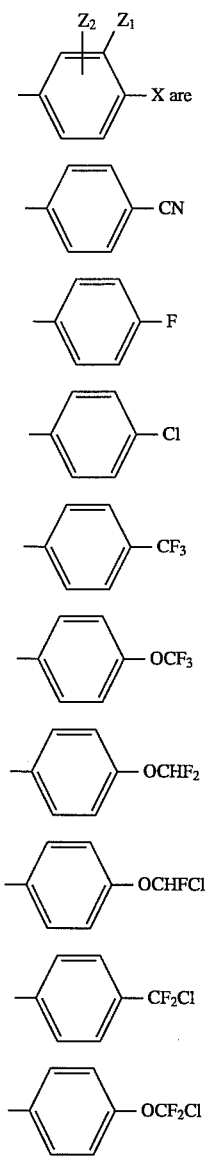

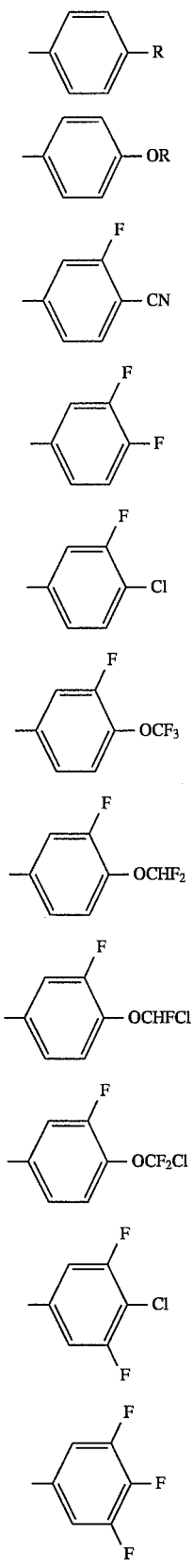

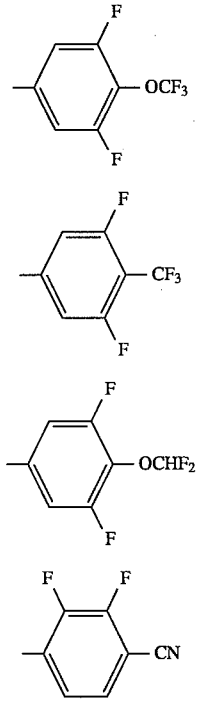

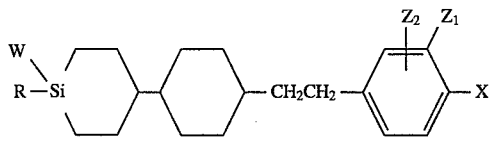

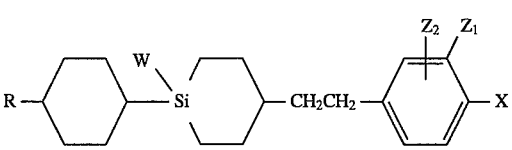

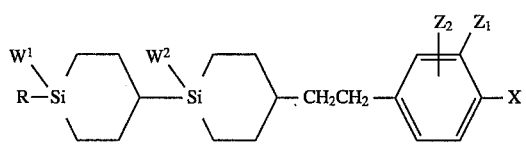

Of these, in terms of their ring structure, the compounds of are preferable for practical use.

For R, the following groups listed in (f) through (j) are desirable for practical use:

(f) A linear-chain alkyl group with a carbon number of 3–7, i.e. a n-propyl, n-butyl, n-pentyl, n-hexyl or n-heptyl group (g) Some mono- or di-fluoroalkyl groups with a carbon number of 1–10 including 2-fluoroethyl, 2-fluoropropyl, 2-fluorobutyl, 2-fluoropentyl, 2-fluorohexyl, 2-fluoroheptyl, 4-fluorobutyl, 4-fluoropentyl, 4-fluorohexyl, 4-fluoroheptyl, 5-fluoropentyl, 5-fluorohexyl, 5-fluoroheptyl, 6-fluorohexyl, 6-fluoroheptyl, 7-fluoroheptyl, 2,2-difluoroethyl, 2,2-difluoropropyl, 2,2-difluorobutyl, 2,2-difluoropentyl, 2,2-difluorohexyl, 2,2-difluoroheptyl, 4,4-difluorobutyl, 4,4-difluoropentyl, 4,4-difluorohexyl, 4,4-difluoroheptyl, 5,5-difluoropentyl, 5,5-difluorohexyl, 5,5-difluoroheptyl, 6,6-difluorohexyl, 6,6-difluoroheptyl, and 7,7-difluoroheptyl groups (h) Some branched-chain alkyl groups including isopropyl, 1-methylpropyl, 2-methylpropyl, 1-methylbutyl, 2-methylbutyl, 3-methylbutyl, 1-methylpentyl, 2-methylpentyl and 2-ethylhexyl groups (i) An alkoxyalkyl group with a carbon number of 2–6, i.e. a methoxymethyl, methoxyethyl, methoxypropyl, methoxypentyl, ethoxymethyl, ethoxyethyl, propoxymethyl or pentoxymethyl group (j) Some alkenyl groups including vinyl, 1-propenyl, 3-butenyl, 1-pentenyl, 3-pentenyl, 4-pentenyl, 1-hexenyl, 5-hexenyl, 6-heptenyl and 7-octenyl groups H, F and $CH_3$ groups are desirable for W, $W^1$ and $W^2$ in practical use.

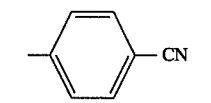

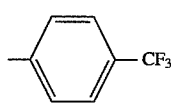

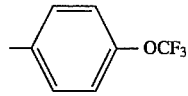

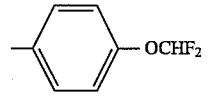

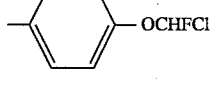

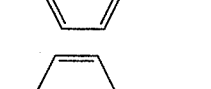

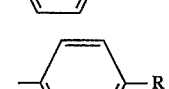

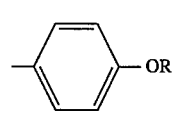

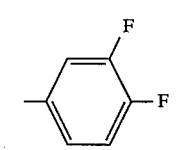

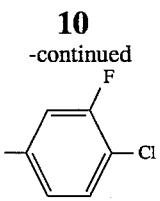

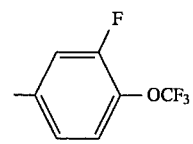

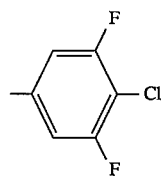

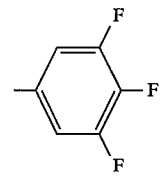

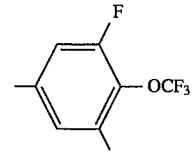

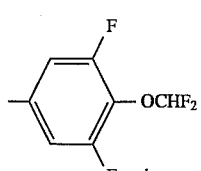

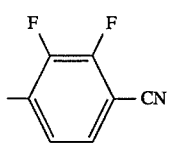

F and

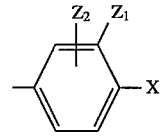

are desirable in practical use for $$\underset{}{\underset{}{\bigcirc}}\overset{Z_2\ Z_1}{\phantom{X}}-X$$

These compounds are prepared by a carbon-carbon bond formation reaction or carbon-silicon bond formation reaction between an organometallic reagent and a compound which has an eliminatable group(s) such as a halogen atom, alkoxy, methanesulfonyl, trifluoromethanesulfonyl, benzenesulfonyl or p-toluenesulfonyl group. A detailed description is given below.

In the reaction between the organometallic reagent

R—M and

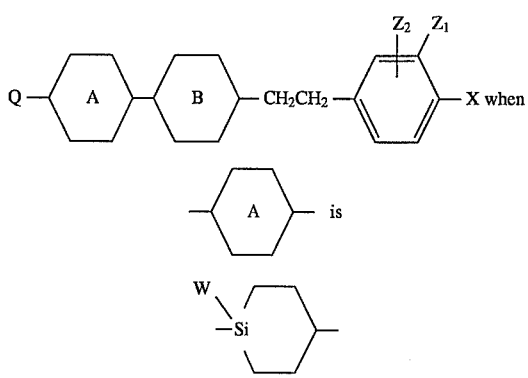

(W denotes H, F or CH3 group), Q is a halogen atom or an alkoxy group, for example. Particularly, if Q is a Cl or Br atom, or an OCH$_3$ or OCH$_2$CH$_3$ group, then the carbon-silicon bond formation reaction proceeds easily and gives a high yield of the target product.

Also, when

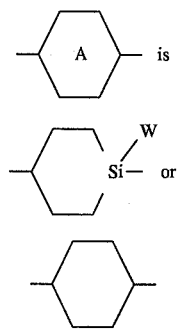

this carbon-carbon bond formation reaction is carried out in the presence of a catalytic amount of copper salt. In this case, Q is a halogen atom or a methanesulfonyl, trifluoromethanesulfonyl, benzenesulfonyl or p-toluenesulfonyl group, for example. It is particularly preferable if Q is Br or I because then the target product can be obtained with a high yield.

In the reactions between an organometallic reagent

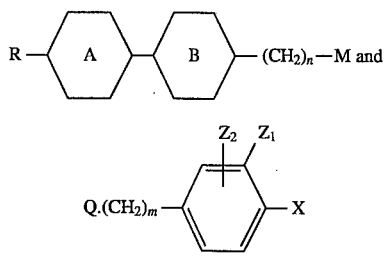

if (m, n)=(2, 0) or (1, 1), then these carbon-carbon bond formation reactions are carried out in the presence of a catalytic amount of copper salt. MgP (P denotes a halogen atom), ZnP or Li can be used for M. Compounds such as a halogen atom or a methanesulfonyl, trifluoromethanesulfonyl, benzenesulfonyl or p-toluenesulfonyl group can be used for Q. It is particularly preferable if Q is Br, I or p-toluenesulfonyl group because then the target product can be obtained with a high yield.

When (m, n)=(0, 2), this reaction is carried out in the presence of a transition metal catalyst. Palladium compounds and nickel compounds are particularly preferable for the catalyst. Examples of the palladium catalysts are zero-valent palladium compounds such as tetrakis (triphenylphosphine) palladium (0) and di [1,2-bis (diphenylphosphino) ethane] palladium (0), divalent palladium compounds such as palladium acetate and palladium chloride and complex compounds composed of these and ligands, as well as a combination of these divalent palladium compounds and a reducing agent. Examples of the nickel catalysts are divalent nickel compounds such as 1,2-bis (diphenylphosphino) ethane nickel (II) chloride, 1,3-bis (diphenylphosphino) propane nickel (II) chloride, and bis (triphenylphosphine) nickel (II) chloride, and zero-valent nickel compounds such as tetrakis (triphenylphosphine) nickel (0). It is particularly preferable if Q is Cl, Br or I because then the target product can be obtained with a high yield.

In the reactions between an organometallic reagent

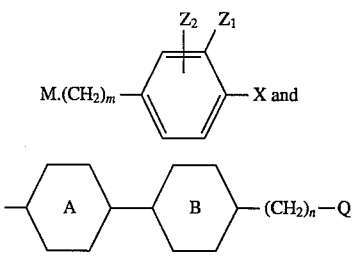

these carbon-carbon bond formation reactions are carried out in the presence of a catalytic amount of copper salt. A halogen atom or a methanesulfonyl, trifluoromethanesulfonyl, benzenesulfonyl or p-toluenesulfonyl group can be used for Q. It is particularly preferable if Q is Br, I or p-toluenesulfonyl group because then the target product can be obtained with a high yield.

In the reactions between an organometallic reagent

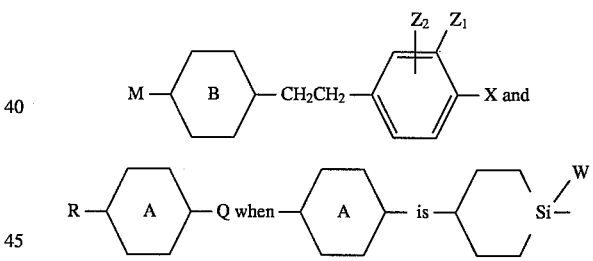

Q is a halogen atom or an alkoxy group, for example. It is particularly preferable if Q is a Cl or Br atom, or an OCH$_3$ or OCH$_2$CH$_3$ group, because then the carbon-silicon bond formation reaction proceeds easily and gives a high yield of the target product.

If

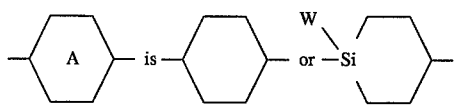

(W denotes H, F or CH$_3$ group), then this carbon-carbon bond formation reaction is carried out in the presence of a catalytic amount of copper salt. In this case, Q is a halogen atom or a methanesulfonyl, trifluoromethanesulfonyl, benzenesulfonyl or p-toluenesulfonyl group, for example. It is particularly preferable if Q is Br, I or p-toluenesulfonyl group because then the target product can be obtained with a high yield.

In the reaction between the organometallic reagent

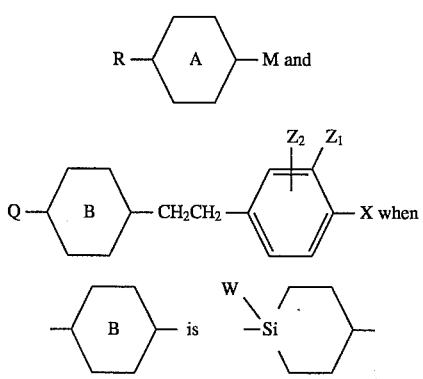

Q is a halogen atom or an alkoxy group, for example. It is particularly preferable if Q is a Cl or Br atom, or an OCH$_3$ or OCH$_2$CH$_3$ group, because then the carbon-silicon bond formation reaction proceeds easily and gives a high yield of the target product.

If

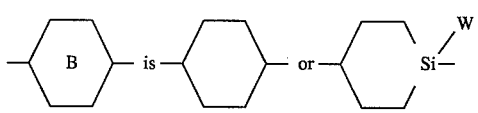

then this carbon-carbon bond formation reaction is carried out in the presence of a catalytic amount of copper salt. In this case, Q is a halogen atom or a methanesulfonyl, trifluoromethanesulfonyl, benzenesulfonyl or p-toluenesulfonyl group, for example. It is particularly preferable if Q is Br, I or p-toluenesulfonyl group because then the target product can be obtained with a high yield.

Since the compound produced here is a mixture of trans isomers and cis isomers in terms of the conformation of the silacyclohexane ring, a conventional purification means such as chromatography and recrystallization is employed to separate and purify the trans isomers to obtain the silacyclohexane compound represented by the general formula (I) of this invention.

The silacyclohexane compound of this invention can be mixed with known compounds to obtain a liquid crystal composition. The compound used for mixing to obtain the liquid crystal compound can be chosen from among the known compounds shown below:

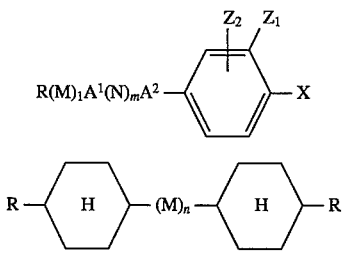

In the above formulas, (M) and (N) denote one of 1) through 5) shown below:

1) A trans-1,4-cyclohexylene group which has no substitution or which has one or more substitutional groups such as F, Cl, Br, CN or alkyl groups
2) A trans-1,4-cyclohexylene group in which 0 or S is substituted for one or nonadjacent two CH$_2$ groups in the cyclohexane ring
3) A 1,4-cyclohexenylene group
4) A 1,4-phenylene group which has no substitution or which has one or two substitutional groups such as F, Cl, CH$_3$ or CN groups
5) A 1,4-phenylene group in which an N atom is substituted for one or two CH groups in the ring $A^1$ and $A_2$ denote —CH$_2$CH$_2$—, —CH=CH—, —C$\triangledown$C—, —CO$_2$—, —OCO—, —CH$_2$O—, —OCH$_2$— or a single bond l, m=0, 1 or 2 (where l+m=1, 2 or 3), and n =0, 1 or 2.

R denotes hydrogen, a linear-chain alkyl group with a carbon number of 1–10, a mono- or di-fluoroalkyl group with a carbon number of 1–10, a branched-chain alkyl group with a carbon number of 3–8, an alkoxyalkyl group with a carbon number of 2–7, or an alkenyl group with a carbon number of 2–8.

X denotes a CN, F, Cl, CF$_3$, OCF$_3$, OCHF$_2$, OCHFCl, CF$_2$Cl, OCF$_2$Cl, R or OR group. $Z_1$ denotes H, F or Cl. $Z_2$ denotes H or F.

In the above description, if l=2 and n=2, then (M) can contain heterogeneous rings, and if m=2, then (N) can contain heterogeneous rings.

The ratio of one or more types of the silacyclohexane compound of this invention contained in the liquid crystal phase is 1–50wt %, more preferably 5–30 wt %. The liquid crystal composition can also contain a polygenetic dye(s) to generate a colored guest-host system and additives to change the dielectric anisotropy, viscosity and the orientation of the nematic phase.

The liquid crystal composition thus formed is sealed between transparent plates which have electrodes of desired shapes and is thus used as liquid crystal display elements. This element can have various undercoatings, overcoatings for orientation control, a polarizer plate(s), a filter(s) and a reflector layer(s), as necessary. It can be made into a laminated cell or combined with other display elements. Semiconductor substrates and light sources can also be used to make various types of displays.

For the driving method of the liquid crystal display element, prior-art methods in the industry of liquid crystal display elements, such as the dynamic scattering (DSM) method, the twisted nematic (TN) method, the super twisted nematic (STN) method, the polymer dispersion (PD) method and the guest-host (GH) method can be adopted.

EXAMPLE

The details of this invention are described below by referring to specific examples.

Example 1

Preparation of trans-4-(trans-4-(2-(3,4-difluorophenyl) ethyl) cyclohexyl)-1-n-propyl-1-silacyclohexane 2.5 g (20 mmol) of n-propyl bromide was dripped into a mixture of 0.5 g (21 mmol) of magnesium and 50 ml of tetrahydrofuran (hereafter referred to as "THF") to obtain a Grignard's reagent. This solution was then dripped into a 50 ml THF solution of 7.4 g of 1-chloro-4-(trans-4-(2-(3,4-difluorophenyl) ethyl) cyclohexyl)-1-silacyclohexane. The silacyclohexane rings of the product thus obtained were a mixture of trans isomers and cis isomers. After a conventional after treatment, they were separated by means of chromatography to obtain 5.8 g (yield 80%) of trans-4-(trans-4-(2-(3,4-difluorophenyl) ethyl) cyclohexyl)-1-n-propyl-1-silacyclohexane.

IR ν max: 2920, 2852, 2100, 1520, 1286, 887 and 818 cm$^{-1}$. C—S transition temperature: 7.6° C., S—N transition temperature: 18.5° C., N—I transition temperature: 74.8° C.

Example 2

Using the same process as Example 1, trans-4-(trans-4-(2-(3,4,5-trifluorophenyl) ethyl) cyclohexyl)-1-n-pentyl-1-silacyclohexane was obtained.

IR ν max:2922, 2852, 2100, 1620, 1531, 1446, 1352, 1234, 1041, 835cm$^{-1}$ C—N transition temperature: 21.9° C. N—I transition temperature: 57.8° C.

Example 3

Using the same process as Example 1, trans-4-(trans-4-(2-(4-trifluoromethoxyphenyl) ethyl) cyclohexyl)-1-n-propyl-1-fluoro-1-silacyclohexane was obtained.

Example 4

Using the same process as Example 1, trans-4-(trans-4-(2-(4-trifluoromethoxyphenyl) ethyl) cyclohexyl)-1-n-pentyl-1-silacyclohexane was obtained.

Example 5

Using the same process as Example 1, trans-4-(trans-4-(2-(4-chloro-3-fluorophenyl) ethyl) cyclohexyl)-1-n-propyl-1-methyl-1-silacyclohexane was obtained.

Example 6

Using the same process as Example 1, trans-4-(trans-4-(2-(4-fluorophenyl) ethyl) cyclohexyl)-1-n-pentyl-1-silacyclohexane was obtained.

Example 7

Using the same process as Example 1, trans-4-(trans-4-(2-(4-chlorophenyl) ethyl) cyclohexyl)-1-n-pentyl-1-silacyclohexane was obtained.

Example 8

Using the same process as Example 1, trans-4-(trans-4-(2-(4-cyanophenyl) ethyl) cyclohexyl)-1-n-pentyl-1-silacyclohexane was obtained.

Example 9

Using the same process as Example 1, trans-4-(trans-4-(2-(3,4-difluorophenyl) ethyl) cyclohexyl)-1-allyl-1-silacyclohexane was obtained.

Example 10

Using the same process as Example 1, trans-4-(trans-4-(2-(4-fluorophenyl) ethyl) cyclohexyl)-1-(3-methoxypropyl)-1-silacyclohexane was obtained.

Example 11

Preparation of trans-1-(trans-4-n-propylcyclohexyl)-4-(2-(4-fluorophenyl) ethyl)-1-silacyclohexane 6.3 g (20 mmol) of trans-1-(trans-4-n-propylcyclohexyl)-4-bromomethyl-1-silacyclohexane was dripped into a mixture of 0.5 g (21 mmol) of magnesium and 50 ml of THF to obtain a Grignard's reagent. This solution was then dripped into a 50 ml THF solution of 50 mg of triethylphosphate, 10 mg of copper iodide (I) and 3.9 g (20 mmol) of p-fluorobenzyl bromide. After a conventional after treatment, 6.1 g (yield 85%) of trans-1-(trans-4-n-propylcyclohexyl)-4-(2-(4-fluorophenyl) ethyl)-1-silacyclohexane was obtained.

IR ν max: 2916, 2841, 2089, 1510, 1223, 891 and 820 cm$^{-1}$. C—N transition temperature: 39.9° C., N—I transition temperature: 56.7° C.

Example 12

Using the same process as Example 11, trans-4-(trans-4-ethylcyclohexyl)-1-(2-(4-fluorophenyl) ethyl)-1-silacyclohexane was obtained.

Example 13

Using the same process as Example 11, trans-1-(trans-4-n-propylcyclohexyl)-4-(2-(3,4-difluorophenyl) ethyl)-1-silacyclohexane was obtained.

Example 14

Using the same process as Example 11, trans-4-(trans-4-(2-(3-fluoro-4-trifluoromethoxyphenyl) ethyl) cyclohexyl)-1-n-pentyl-1-silacyclohexane was obtained.

Example 15

Using the same process as Example 11, trans-4-(trans-4-(2-(4-fluorophenyl) ethyl) cyclohexyl)-1-n-propyl-1-silacyclohexane was obtained.

IR ν max: 2918, 2850, 2100, 1512, 1232, 887 and 823 cm$^{-1}$. C—N transition temperature: 18.3° C., S—N transition temperature: 63.5° C., N—I transition temperature: 98.4° C.

Example 16

Using the same process as Example 11, trans-4-(trans-4-(2-(4-fluorophenyl) ethyl)-1-silacyclohexyl)-1-n-pentyl-1-silacyclohexane was obtained.

Example 17

Using the same process as Example 11, trans-4-(trans-4-n-pentylcyclohexyl)-1-(2-(3,4-difluorophenyl) ethyl)-1-methyl-1-silacyclohexane was obtained.

Example 18

Using the same process as Example 11, trans-4-(trans-4-(2-(4-methoxyphenyl ) ethyl ) cyclohexyl )-1-n-pentyl-1-silacyclohexane was obtained.

Example 19

Using the same process as Example 11, trans-1-(trans-4-n-propylcyclohexyl)-4-(2-(3,5-difluoro-4-difluoromethoxyphenyl) ethyl)-1-silacyclohexane was obtained.

Example 20

Using the same process as Example 11, trans-4-(trans-4-(2-(4-propylphenyl) ethyl) cyclohexyl)-1-n-propyl-1-silacyclohexane was obtained.

Example 21

Preparation of trans-4-(trans-4-(2-(4-trifluoromethoxyphenyl) ethyl) cyclohexyl)-1-n-propyl-1-silacyclohexane 4.8 g (20 mmol) of p-trifluoromethoxybromobenzene was dripped into a mixture of 0.5 g (21 mmol) of magnesium and 50 ml of THF to obtain a Grignard's reagent. This solution was then dripped into a 50 ml THF solution of 10 mg of copper chloride (I), 10 mg of copper chloride (II) and 7.3 g (20 mmol) of trans-4-(2-bromoethyl) cyclohexyl)-1-n-propyl-1-silacyclohexane. After a conventional after treatment, 6.6 g (yield 80%) of trans-4-(trans-4-(2-(4-trifluoromethoxyphenyl) ethyl) cyclohexyl)-1-n-propyl-1-silacyclohexane was obtained.

Example 22

Using the same process as Example 21, trans-1-(trans-4-(2-(4-fluorophenyl) ethyl) cyclohexyl)-4-n-pentyl-1-silacyclohexane was obtained.

Example 23

Using the same process as Example 21, trans-1-(trans-4-n-pentylcyclohexyl)-4-(2-(4-fluorophenyl) ethyl)-1-silacyclohexane was obtained.

IR ν max: 2916, 2845, 2094, 1510, 1223, 887 and 823 $cm^{-1}$. C—N transition temperature: 21.3° C., N—I transition temperature: 67.1° C.

Example 24

Using the same process as Example 21, trans-4-(trans-4-n-propylcyclohexyl)-1-(2-(4-fluorophenyl) ethyl)-1-silacyclohexane was obtained.

Example 25

Preparation of trans-4-(trans-4-(2-(4-fluorophenyl) ethyl) cyclohexyl)-1-iso-butyl-1-silacyclohexane 5.7 g (20 mmol) of 4-(p-fluorophenyl) cyclohexybromide was dripped into a mixture of 0.5 g (21 mmol) of magnesium and 50 ml of THF to obtain a Grignard's reagent. This solution was then dripped into a 50 ml THF solution of 10 mg of copper iodide (I), 50 mg of triethylphosphate and 4.7 g (20 mmol) of 4-bromo-1-iso-butyl-1-silacyclohexane. The silacyclohexane rings of the reacted mixture thus obtained were a mixture of trans isomers and cis isomers. After a conventional after treatment, they were separated by means of chromatography to obtain 4.7 g (yield 65%) of trans-4-(trans-4-(2-(4-fluorophenyl) ethyl) cyclohexyl)-1-iso-butyl-1-silacyclohexane.

Example 26

Using the same process as Example 25, trans-1-(trans-4-(2-(3,4-difluorophenyl) ethyl) cyclohexyl)-4-n-pentyl-1-silacyclohexane was obtained.

Example 27

Preparation of trans-4-(trans-4-(2-(3,4-difluorophenyl) ethyl) cyclohexyl)-1-n-pentyl-1-silacyclohexane 5.0 g (20 mmol) of 1-n-pentyl-4-bromo-1-silacyclohexane was dripped into a mixture of 0.5 g (21 mmol) of magnesium and 50 ml of THF to obtain a Grignard's reagent. This solution was then dripped into a 50 ml THF solution of 6.1 g (20 mmol) of 4-(3,4-difluorophenetyl)-1-bromocyclohexane. The products obtained were separated by means of chromatography to obtain 6.5 g (yield 80%) of trans-4-(trans-4-(2-(3,4-difluorophenyl) ethyl) cyclohexyl)-1-n-pentyl-1-silacyclohexane.

Example 28

Using the same process as Example 27, trans-1-(trans-4-n-butylcyclohexyl)-4-(2-(4-florophenyl) ethyl)-1-silacyclohexane was obtained.

Example 29

Preparation of trans-4-(trans-4-(2-(3,4,5-trifluorophenyl) ethyl) cyclohexyl)-1-n-propyl-1-silacyclohexane 2.5 g (20 mmol) of n-propyl bromide was dripped into a mixture of 0.5 g (21 mmol) of magnesium and 50 ml of THF to obtain a Grignard's reagent. This solution was then dripped into a 50 ml THF solution of 7.8 g (20 mmol) of 1-chloro-4-(trans-4-(2-(3,4,5-trifluorophenyl) ethyl) cyclohexyl)-1-silacyclohexane. The silacyclohexane rings of the reacted mixture thus obtained were a mixture of trans isomers and cis isomers. After a conventional after treatment, they were separated by means of chromatography to obtain 6.1 g (yield 80%) of trans-4-(trans-4-(2-(3,4,5-trifluorophenyl) ethyl) cyclohexyl)-1-n-propyl- 1-silacyclohexane.

IR(KBr disc) ν max:2922, 2852, 2100, 1620, 1531, 1446, 1352, 1234, 1041,845 $cm^{-1}$ C—S transition temperature: 11.9° C., S—N transition temperature: 19.6° C., N—I transition temperature: 58.6° C.

Example 30

Preparation of trans-4-(trans-4-(2-(4-fluorophenyl) ethyl) cyclohexyl)-1-n-pentyl- 1-silacyclohexane 3.1 g (20 mmol) of n-propyl bromide was dripped into a mixture of 0.5 g (21 mmol) of magnesium and 50 ml of THF to obtain a Grignard's reagent. This solution was then dripped into a 50 ml THF solution of 6.8 g (20 mmol) of 1-chloro-4-(trans-4-(2-(4-fluorophenyl) ethyl) cyclohexyl)-1-silacyclohexane. The silacyclohexane rings of the reacted mixture thus obtained were a mixture of trans isomers and cis isomers. After a conventional after treatment, they were separated by means of chromatography to obtain 6.4 g (yield 85%) of trans-4-(trans-4-(2-(4-fluorophenyl) ethyl) cyclohexyl)-1-n-pentyl-1-silacyclohexane.

C—S transition temperature: 21.3° C., N—I transition temperature: 67.1° C.

Example 31

Preparation of trans-4-(trans-4-(2-(3,4-difluorophenyl) ethyl) cyclohexyl)-1-(4-pentenyl)-1-silacyclohexane 3.0 g (20 mmol) of 4-bromopentene was dripped into a mixture of 0.5 g (21 mmol) of magnesium and 50 ml of THF to obtain a Grignard's reagent. This solution was then dripped into a 50 ml THF solution of 7.1 g of 1-chloro-4-(trans-4-(2 -(3,4-difluorophenyl) ethyl) cyclohexyl)-1-silacyclohexane. The silacyclohexane rings of the reacted mixture thus obtained were a mixture of trans isomers and cis isomers. After a conventional after treatment, they were separated by means of chromatography to obtain 6.5 g (yield 83%) of trans-4-(trans-4-(2-(3,4-difluorophenyl) ethyl) cyclohexyl)-1-(4-pentenyl)-1-silacyclohexane.

Example 32

Preparation of trans-4-(trans-4-(2-(3,4-difluorophenyl) ethyl) cyclohexyl)-1-(3-methoxypropyl)-1-silacyclohexane 3.1 g (20 mmol) of 3-methoxypropyl bromide was dripped into a mixture of 0.5 g (21 mmol) of magnesium and 50 ml of THF to obtain a Grignard's reagent. This solution was then dripped into a 50 ml THF solution of 7.1 g (20 mmol) of 1-chloro-4-(trans-4-(2-(3,4-difluorophenyl) ethyl) cyclohexyl)-1-silacyclohexane. The silacyclohexane rings of the reacted mixture thus obtained were a mixture of trans isomers and cis isomers. After a conventional after treatment, they were separated by means of chromatography to obtain 6.5 g (yield 81%) of trans-4-(trans-4-(2-(3,4-difluorophenyl) ethyl) cyclohexyl)-1-(3-methoxypropyl)-1-silacyclohexane.

Example 33

Preparation of trans-4-(trans-4-(2-(3,4-difluorophenyl) ethyl) cyclohexyl)-1-(3-methylbutyl)-1-silacyclohexane 3.0 g (20 mmol) of 3-methylbutyl bromide was dripped into a mixture of 0. 5 g (21 mmol) of magnesium and 50 ml of THF to obtain a Grignard's reagent. This solution was then dripped into a 50 ml THF solution of 7.1 g of 1-chloro-4-(trans-4-(2-(3,4-difluorophenyl) ethyl) cyclohexyl)-1-silacyclohexane. The silacyclohexane rings of the reacted mixture thus obtained were a mixture of trans isomers and cis isomers. After a conventional after treatment, they were separated by means of chromatography to obtain 6.9 g (yield 88%) of trans-4-(trans-4-(2-(3,4-difluorophenyl) ethyl) cyclohexyl)-1-(3-methylbutyl)-1-silacyclohexane.

The compounds of this invention obtained in the examples described above were added to existing liquid crystal compositions to prepare liquid crystal compositions of this invention.

Example 34

A liquid crystal mixture comprising 34% of 2-(trans-4-n-pentylcyclohexyl)-1-(3,4-difluorophenyl) ethane, 15% of 1,2-difluoro-4-[trans-4-(trans-4-n-propylcyclohexyl) cyclohexyl] benzene and 51% of 2-[trans-4-(trans-4-propylcyclohexyl) cyclohexyl]-1-(3,4-difluorophenyl) ethane exhibits the nematic liquid crystal phase in the temperature range of −17° to 63° C. A liquid crystal mixture comprising 60% of this mixture and 40 wt % of trans-4-(trans-4-(2-(3,4-difluorophenyl) ethyl) cyclohexyl)-1-n-propyl-1-silacyclohexane obtained in Example 1 exhibits a C—N transition point of −27° C. and a N—I transition point of 70° C.

The liquid crystal compounds of this invention with Si as a ring composing element have an extended nematic liquid crystal phase. Also, liquid crystal compounds whose X in the general formula (I) is a group other than R or OR have, in addition to the advantages mentioned above, the effect of lowering the threshold voltage because of a greater dielectric anisotropy.

The liquid crystal compounds of this invention, depending on the selection of the substitutional groups, can be widely used as the base material which comprises the major component of the liquid crystal phase, in a manner similar to how the conventional liquid crystal compounds with a ECCP structure of similar hydrocarbon rings are used. The liquid crystal compound whose substitutional group X in the general formula (I) is R or OR has near-zero dielectric anisotropy, and therefore it should preferably be used for the liquid crystal phase for display based on dynamic scattering (DS) or deformation of aligned phase (DAP mode). The compounds in which X is other than R or OR should preferably be used for manufacturing the liquid crystal phase with a large positive dielectric anisotropy which is used in display elements based on the twisted nematic cell or the cholesteric-nematic phase transition.

We claim:

1. A silacyclohexane compound represented by the following general formula (1):

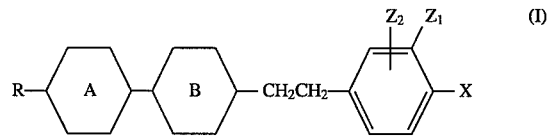

wherein R denotes a linear-chain alkyl group with a carbon number of 1–10, a mono- or di-fluoroalkyl group with a carbon number of 1–10, a branched-chain alkyl group with a carbon number of 3–8, an alkoxyalkyl group with a carbon number of 2–7, or an alkenyl group with a carbon number of 2–8, and at least one of

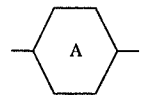

and

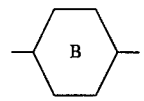

denotes a trans-1-sila-1,4-cyclohexylene or a trans-4-sila-1,4-cyclohexylene group whose silicon at position 1 or position 4 has a substitutional group(s) of H, F, Cl or $CH_3$ and the other is a trans-1,4-cyclohexylene group. X denotes a CN, F, Cl, $CF_3$, $OCF_3$, $OCHF_2$, $OCHFCl$, $CF_2Cl$, $OCF_2Cl$, R or OR group, $Z_1$ denotes H, F or Cl, and $Z_2$ denotes H or F.

2. A method of preparing the silacyclohexane compound as described in claim 1, wherein a carbon-carbon bond formation reaction or a carbon-silicon bond formation reaction is used between an organometallic reagent R—M, wherein Q denotes MgP (P denotes a halogen atom), ZnP or Li, and

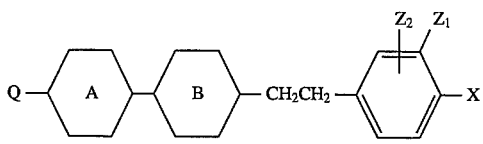

wherein Q denotes a halogen atom, or an alkoxy, methanesulfonyl, trifluoromethanesulfonyl, benzenesulfonyl or p-toluenesulfonyl group.

3. A method of preparing the silacyclohexane compound as described in claim 1, wherein a carbon-carbon bond formation reaction or a carbon-silicon bond formation reaction is used between an organometallic reagent

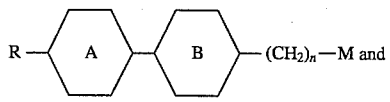

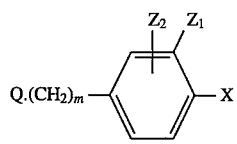

wherein each of n and m denotes an integer 0, 1 or 2, where n+ m=2.

4. A method of preparing the silacyclohexane compound as described in claim 1, wherein a carbon-carbon bond formation reaction or a carbon-silicon bond formation reaction is used between an organometallic reagent

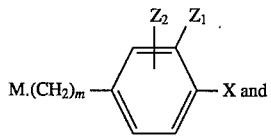

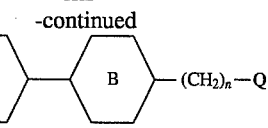

5. A method of preparing the silacyclohexane compound as described in claim 1, wherein a carbon-carbon bond formation reaction or a carbon-silicon bond formation reaction is used between an organometallic reagent

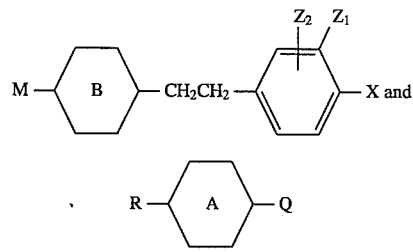

6. A method of preparing the silacyclohexane compound as described in claim 1, wherein a carbon-carbon bond formation reaction or a carbon-silicon bond formation reaction is used between an organometallic reagent

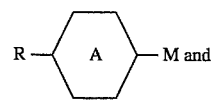

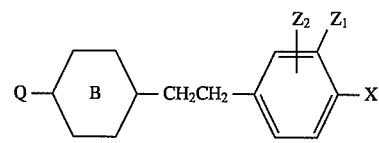

7. A liquid crystal composition comprising the silacyclohexane compound of claim 1.

* * * * *